United States Patent [19]

Köstlin et al.

[11] 4,431,919
[45] Feb. 14, 1984

[54] DETECTION APPARATUS, PARTICULARLY FOR USE IN LIQUID CHROMATOGRAPHY

[75] Inventors: Heiner Köstlin; Manfred Peterek, both of Aachen; Hartwig Schaper, Rötgen, all of Fed. Rep. of Germany; Robert J. Dolphin, Cambridgeshire; Frederick W. Willmott, Grinstead Sussex, both of England

[73] Assignee: U.S. Philips Corporation, New York, N.Y.

[21] Appl. No.: 252,722

[22] Filed: Apr. 10, 1981

[30] Foreign Application Priority Data

Apr. 10, 1980 [DE] Fed. Rep. of Germany ....... 3013765

[51] Int. Cl.³ ..................... G01N 21/76; G01N 27/00
[52] U.S. Cl. ............................. 250/361 C; 73/61.1 C; 422/52; 422/70
[58] Field of Search ............ 250/484.1, 361 C, 458.1, 250/364, 361 R, 459.1; 73/61.1 C; 422/52, 70, 90; 436/172; 204/400, 242

[56] References Cited

U.S. PATENT DOCUMENTS

| | | | |
|---|---|---|---|
| 3,706,381 | 12/1972 | Joynes et al. | 422/70 |
| 3,961,253 | 6/1976 | Brych | 313/358 |
| 4,036,704 | 7/1977 | Takata | 73/61.1 C |
| 4,147,431 | 4/1979 | Mann | 250/458.1 |
| 4,280,815 | 7/1981 | Oberhardt et al. | 436/518 |
| 4,343,767 | 8/1982 | Long et al. | 73/61.1 C |

OTHER PUBLICATIONS

Dallakyan et al., "Method for the Detection of Low Concentrations of Phenols and Substances Containing Sulfhydryl Groups," Gibrbiol Zh., 1978, 14(5), 105-9 (Russ); Chem. Ab., vol. 90, 1979, p. 372, No. 60970.

Primary Examiner—Craig E. Church
Assistant Examiner—Carolyn E. Fields
Attorney, Agent, or Firm—Norman N. Spain

[57] ABSTRACT

A detection apparatus of a simple construction is formed from an electro-chemiluminescence cell (12) having connections for the supply and the discharge of a liquid to be examined, particularly a mobile phase coming from the separation column of a liquid chromatograph, a voltage source (11) and a detector (14) for electric current, which are connected to the electrodes (1, 2) of the cell (12). Preferably a radiation-sensitive element (13) is also provided.

5 Claims, 8 Drawing Figures

DETECTION APPARATUS, PARTICULARLY FOR USE IN LIQUID CHROMATOGRAPHY

The invention relates to a detection apparatus, particularly intended for use in liquid chromatography.

In liquid chromatography the mobile phase, after the chromatographical separation of mixtures of substances, is applied to a detection apparatus for recording the components which were elutriated one after the other from the separation column. German Offenlegungsschrift No. 2522488 and German Offenlegungsschrift No. 2754790 describe the use of an UV-absorption or a fluorescent detection apparatus as the detector. In both cases a large quantity of optical and electronic auxiliary means are required.

The invention has for its object to provide a detection apparatus of a simple construction.

According to the invention, this object is accomplished by means of a detection apparatus which is characterized in that the apparatus comprises an electro-chemiluminescent cell having connections for the supply and the discharge of a liquid to be examined, particularly a mobile phase coming from the separation column of a liquid chromatographic apparatus, and a voltage source and a detector for electric current which are connected to the electrodes of the cell.

A very advantageous embodiment of an apparatus in accordance with the invention is characterized in that the apparatus further comprises a radiation-sensitive element, for example a photocell or photomultiplier.

The invention is based on the idea of employing the principle of electro-chemiluminescence (ECL) for qualitatively and quantitatively detecting chemical substances in a solvent, praticularly in the mobile phase, which comes from the separation column of a liquid chromatograph.

ECL is a luminescence phenomenon which occurs at the reaction of highly energetic reactants (chemiluminescence) which are generated electrochemically. In the most simple case two reactants are formed from the same starting material in accordance with the following reaction formulae:

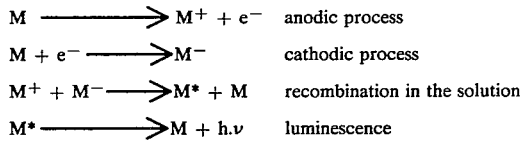

Therein M is, for example, a derivative of a condensed aromatic hydrocarbon, for example from the group of the anthracenes or tetracenes. In view of the extraordinary high reactivity of the electrochemically generated radicalions $M^+$ and $M^-$ and consequently short life, $M^+$ and $M^-$ must be generated in sites which are very close to each other.

In the direct voltage-ECL this is made possible by means of closely positioned electrodes (spacing approximately 1 mm), in the alternating voltage -ECL it is made possible because of the fact that the two types of ions are alternately generated by means of a.c. voltage at the same electrode in rapidly succeeding time intervals (<1 s). In both methods the solution can be made electrically conductive to a very satisfactory extent by the addition of an auxiliary electrolyte.

In a special apparatus it is also possible to generate ECL in solutions having a very poor electric conductivity, that is to say without the addition of a conducting salt. However, for this purpose the spacing between the electrodes must be considerably reduced, namely to some micrometers (J. Electrochem. Soc. 122 (1975), pages 623–640; German patent application No. P 928725.0).

An embodiment in accordance with the invention is shown in the accompanying drawing and will now be further described.

Figure 1:
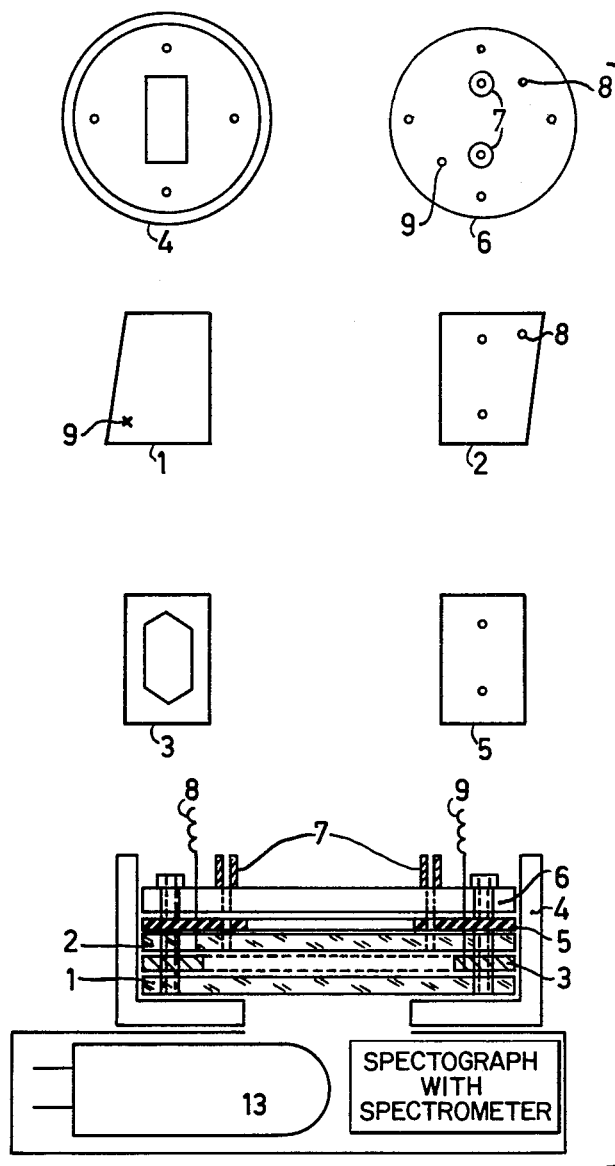
FIG. 1 shows schematically and in a partly cross-sectional view an ECL-cell with radiation-sensitive element, suitable for an apparatus in accordance with the invention, and further shows schematically and on a smaller scale some of the component parts of the ECL-cell in a plan view.

The detection apparatus on the basis of ECL, which will now be described with reference to the drawing is formed from a ECL-cell, a voltage source, a detector (generally a meter) for electric current and a light-sensitive element, generally a photomultiplier. The actual ECL-cell (FIG. 1) consists of two facing flat electrode plates 1 and 2, which together with a base plate 3, a sealing or spacer frame 4 and a pressure plate 6 having a further sealing means 5 are screwed together to form a tight chamber. The pressure plate 6 has bores and connections 7 as an inlet and outlet for the liquid current to be examined; the electrode plate 2 located near the pressure plate 6 also have bore holes to enable the supply and discharge from the space between the electrodes. The base plate 3 has a central opening which faces a photomultiplier 13 a spectrograph with a spectrometer. The electric connection to the electrode plates 1 and 2, respectively is accomplished by contacts 9 and 8, respectively which are located at the edges of the plates 1 and 2, respectively in a diagonal relationship.

The construction described here, which in the form of a thin-layer ECL-cell, requires that the electrode 1 which faces the photomultiplier 13 is transparent; in the embodiment shown this is accomplished by means of a layer of $In_1O_3$:Sn which is pyrolytically deposited on a glass substrate. However, other materials such as $SnO_2$:Sb or very thin metal layers on transparent substrates are suitable. The counter electrode 2 need not be transparent; on the contrary, if said counter electrode reflects to the best possible extent it is ensured that as little as possible of the light emitted in the cell is lost at the counter electrode 2. All metals, either in the form of a thin layer on a substrate (for example a glass substrate) or in the solid form are suitable. In the embodiment a vapour-deposited silver layer on glass was used. It is alternatively possible to combine the pressure plate 6 and the counter electrode 2 to form one component. The spacer frame 4 is made of a thin electrically insulating synthetic material film, approximately 5 to 50 $\mu m$ thick, in this example a film of polytetrafluoroethylene (PTFE) having a thickness of approximately 25 $\mu m$. The contours of the actual ECL-chamber are put in this spacer frame.

Figure 2:
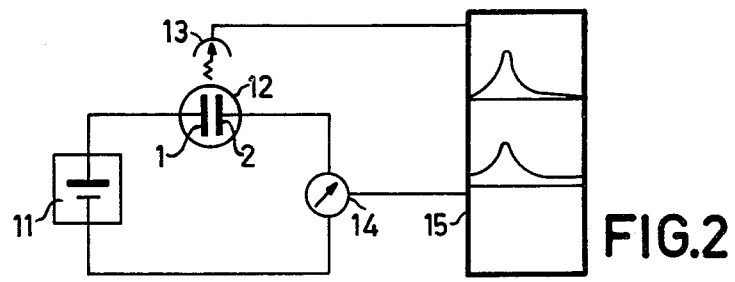
FIG. 2 shows schematically an arrangement of an apparatus in accordance with the invention.

FIG. 2 shows schematically a measuring arrangement. By connecting a voltage supply source 11 to the electrode plates 1 and 2 the solution contained in the cell 12, provided it contains an excitable substance, can be made luminous for the duration of its stay in the cell.

A corresponding photocurrent is then obtained on the photomultiplier 13 and the detector 14 which is in the form of an ammeter simultaneously observes a considerable increase in the electric current flowing through the ECL-cell. Both signals can be recorded by means of a graphic recorder 15 during the flow of the solution. The cell may be operated from a d.c. voltage as well as from an a.c. voltage. In the present example d.c. voltages of approximately 10 Volts were applied, the transparent electrode 1 being preferably connected as the anode for reasons of stability.

The selectivity of the detection apparatus for specific substances can be increased by two measures: 1. The applied d.c. voltage can be matched to the excitation energy of the substances to be detected. Preference is therefore given to an apparatus in accordance with the invention in which the voltage supply is a d.c. voltage source the magnitude of whose voltage is adaptable to the excitation energy of the substances to be detected. 2. A spectral selection of the emitted radiation makes it possible to suppress stray radiation and such a spectral selection may at the same time be used directly as an aid in the identification of the substances. Therefore a very advantageous embodiment of an apparatus in accordance with the invention comprises means for a spectral selection of the emitted radiation, for example a spectrometer of a spectrograph.

With the detection apparatus in accordance with the invention it is possible to detect all substances with which ECL can be generated, particularly compounds from the group of the aromatic hydrocarbons and their derivatives, the heterocyclic compounds, the metal-organic compounds, the dyes, the eximeric and exiplex compounds and the charge transfer complexes. In addition it is also possible to detect with this detection apparatus substances which are indeed not suitable for the ECL, but which can be reduced and/or oxidized electrochemically. In that case the detection of the substances in the cell is effected only on the basis of the changes in the signal of the current detector 14.

In principle, as the solvent there may be employed all aprotic, organic solvents which are inert in the operating conditions of the ECL, for example aromatic hydrocarbons, chlorated alkanes, mono- or polyfunctional ethers, amides, nitriles, sulfoxides or mixtures of these solvents. The solvents must be substantially free of $H_2O$ and $O_2$.

During the experiments which resulted in the invention, 1,2-dimethoxy-ethane (DME) was preferably used as the solvent, which was continuously pumped through the cell by means of a pump (flow rate approximately 1 ml per minute). By means of a metering vale 5 $\mu l$ of a solution in DME of the substance to be detected was injected in each experiment into the solvent stream (1 ml per minute) and the signals produced for some seconds during passage along the ECL cell (volume 5 $\mu l$) were recorded.

In this manner it was, for example, possible to detect rubrene (5,6,11,12-tetraphenyltetracene) in DME in concentrations of $10^{-8}$ mole per liter, which corresponds to a quantity of $2.5.10^{-11}$ g.

The detection apparatus in accordance with the invention has the particular advantages that it is suitable for the analysis of chemical traces, particularly for use in liquid chromatography systems, that its sensitivity is not less than the sensitivity of comparable detectors (UV—, fluorescence-detectors), neither as regards the quantity of substance nor as regards the concentration thereof and that it is of a much simpler implementation.

What is claimed is:

1. A detection apparatus for use with a liquid chromatography apparatus, characterized in that the detection apparatus comprises an electro-chemiluminescence cell (12) having connections (7) for the supply and discharge of a mobile phase coming from the separation column of a liquid chromatography apparatus, two facing electrodes (1, 2), one of which electrodes is transparent, a voltage source (11) and a detector (14) for electric current connected to the electrodes (1, 2) of the cell.

2. A detection apparatus as claimed in claim 1, characterized in that the apparatus further comprises a radiation-sensitive element (13).

3. A detection apparatus as claimed in claim 2, characterized in that the apparatus comprises means for the spectral selection of the radiation emitted from the electro-chemiluminescence cell.

4. A detection apparatus as claimed in claim 1 or 2, characterized in that the voltage source is a d.c. voltage source.

5. A detection apparatus as claimed in claim 4 characterized in that the magnitude of the voltage of the DC source corresponds to the excitation energy of the substance to be detected.

* * * * *